United States Patent [19]

Fenyö

[11] 3,969,571

[45] July 13, 1976

[54] SYSTEM FOR IMPROVING THE EVALUATION OF PICTURES COMPRISING DETAILS HARD TO RECOGNIZE, MAINLY OF FLUOROGRAPHS AND RADIOGRAPHS

[75] Inventor: Martha Fenyö, Budapest, Hungary

[73] Assignee: Medicor Muvek, Budapest, Hungary

[22] Filed: Nov. 5, 1974

[21] Appl. No.: 521,156

[52] U.S. Cl. .................................. 178/6; 178/6.8; 178/DIG. 34
[51] Int. Cl.² .......................................... H04N 5/14
[58] Field of Search .................. 178/DIG. 34, 6, 6.8

[56] References Cited
UNITED STATES PATENTS

| | | | |
|---|---|---|---|
| 3,030,442 | 4/1962 | Brandle | 178/6.8 |
| 3,441,667 | 4/1969 | Novacek | 178/6.8 |
| 3,535,443 | 10/1970 | Rieke | 178/6.8 |

*Primary Examiner*—Robert L. Griffin
*Assistant Examiner*—Edward L. Coles
*Attorney, Agent, or Firm*—Young & Thompson

[57] ABSTRACT

A circuit arrangement for the transmission of picture details through a video chain emphasizes blurred contours and is connected in series with a section serving for the transmission of video signals separated from the synchronized signals of the video chain. The circuit arrangement contains delay means having a tapping point, an adder, and a frequency-independent level control unit that connects the input of the delay means to the first input of the adder. The frequency-independent level control unit is connected between the tapping point and the second input of the adder, and the output of the delay means is connected to the third input of the adder. The first and third inputs of the adder belong to an operation having a common sign opposite to that of the second input, and its input is formed by the input point of the delay means. The output is formed by the output of the adder.

4 Claims, 4 Drawing Figures

SYSTEM FOR IMPROVING THE EVALUATION OF PICTURES COMPRISING DETAILS HARD TO RECOGNIZE, MAINLY OF FLUOROGRAPHS AND RADIOGRAPHS

The invention relates to a system for improving evaluation of pictures comprising details hard to recognize, particularly of fluorographs, radiographs, microscope pictures as well as of photos taken therefrom.

In the known X-ray picture display system only the contrast and brightness values can be adjusted, equally if a radiograph or a picture on the fluorescent screen is concerned. This restricted possibility of adjustment, however, proved to be insufficient to emphasise all important details of a structure appearing on the X-ray picture and to suppress unimportant details, though just this kind of adjustment would be necessary to an effective evaluation of X-ray pictures. If e.g. a radiograph for diagnostical purpose is to be evaluated, these adjustments are necessary not only for ensuring a wider contrast range, or for changing the brightness of the picture, but these adjustments are necessary to make visible also the smallest details in order to help in getting a more accurate diagnosis; while in other cases, where the contours, the extent and shape of greater details are of highest importance, the display of small details are even irrelevant, disturbing only the diagnostician.

In a known system for solving this problem two video-cameras are applied to make two independent sequences of video-signals from the examined radiographs and these signals are first added or mixed than fed to a display monitor. By using this method, the structural richness of the pictures can be adjusted generally in on a few steps.

The drawback of such known systems is their extremely high price and complicated design, while the adjustment of the structural richness can be realized only in a small number of steps. It should be added thereto that to apply the aforementioned method, two radiographs must be taken in rapid sequence from the same area, from these two pictures respective video-signal sequences are to be produced by applying two independent TV cameras, the video-signal sequences should be synchronized and through a differential or mixer amplifier transmitted to a display monitor. Considering all these steps, it will be easy to see that said facilities are expensive, very complicated and yet, they do not render appropriate help to the diagnostician.

The object of the invention is to provide a display by which the picture details, even the faint ones, required for the picture evaluation, particularly the contours of said details can be emphasized.

Another object of the invention is to provide a display by which, besides increasing the structural richness of the required details, the picture dynamics corresponding to the original brightness range of any chosen detail on the examined picture can be expanded.

Yet another object of the invention is to provide a display system, capable of optimal sharpening of the required picture details in which the extent of the sharpening and the size of these details can be adjusted to the required values by using continuous regulation.

The radical idea of the invention is based on the Fourier-analysis. According to this widely known principle all periodic functions can be decomposed into different sine oscillations, since even the most complex periodic function can be obtained from the superposition of individual sine oscillations. If the video-singal sequence of an X-ray picture (taken by means of a TV camera) is regarded as a harmonic function, it can also be considered as a superposition of individual sine functions having different frequencies and amplitudes. It is clear that the high frequency components correspond to the smaller picture details, while the lower frequency components correspond to the details having greater size.

If a frequency selective filtering step is inserted within the video transmission path, in which the lower frequency components are suppressed, the resulted picture will be richer in details, while if the high frequency components are suppressed, a picture with greater details will appear on the screen, but the contours of these greater details will be better outlined.

In the picture detail emphasizing method according to a first aspect of the invention a standard video-signal sequence is made from the examined picture by using only one TV camera, the natural spectral distribution of said video-signals is electronically modified according to a predetermined frequency response defined within the video frequency range and the modified video-signals are displayed on a screen.

Independent of the aforementioned method or together with it, according to a second aspect of the invention the evaluation of the examined picture details can be further improved in which a standard video-signal sequence is made from the examined picture using electronic scanning technique employing only one camera, the video-signal sequence is displayed on a screen, wherein the brightness range corresponding to the relevant details of the examined picture is extended on the displayed picture at the expense of the brightness range of the irrelevant details by using a continuous brightness dynamic expansion technique.

The expression brightness dynanaic means the full width of the brightness range on the examined picture detail extending between the most and the least faint gradations.

This modification of the frequency response can be performed according to a third aspect of the invention by a system including a single TV camera for producing standard video-signals from the examined picture and a display unit, wherein a frequency filter is connected in series with a path extending between said camera and the display unit to modify the video frequency response; the filter includes an adder having at least two inputs; the output of the adder is coupled to the display unit, its first input forming the input of the frequency filter; a frequency dependent means and in series with this means a frequency independent level adjusting means are connected between the first and second input of the adder; the control of the adjusting means providing changes in the extent of the frequency response modification.

In respect of said process it is immaterial, whether the examined picture is available in the form of a fluorograph, a radiograph, a microscope picture or any other kind of picture, since only one condition is imposed upon the picture chosen to be examined that is it shall be suitable for electronic scanning. It must be understood therefore that the invention cannot be restricted to any special field of application where these pictures are used, because it can be used for the elaluation of any picture comprising faint or poor details. The invention will be further described by way of examples, with reference to the accompanying drawings, in which:

FIG. 1 shows the schematic block diagram of the system according to the invention, in which a radiograph 2 is transilluminated by a light source 1.

Figure 1:
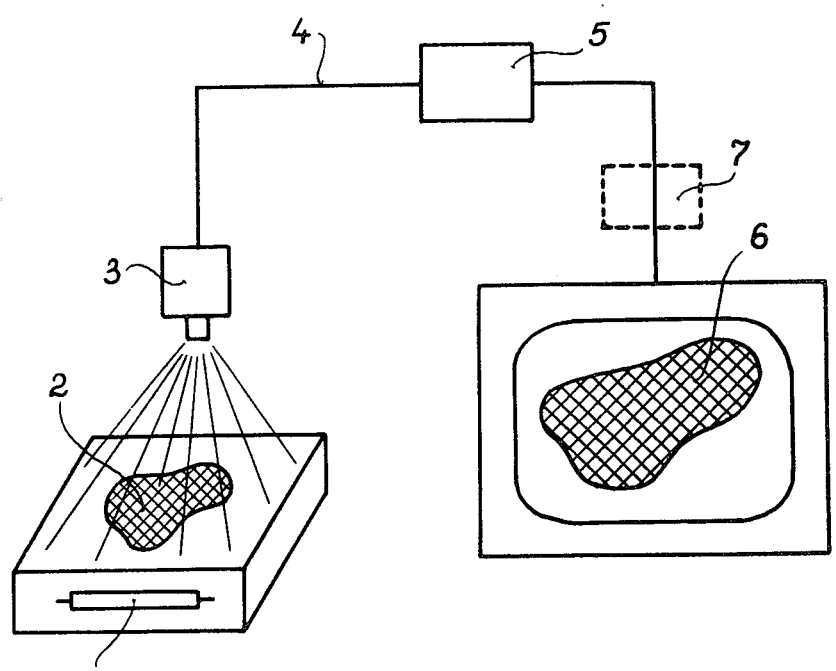
FIG. 1 is a simplified schematic block diagram of the system according to the invention.

From the radiograph 2 a TV camera 3 makes standard video sequences. The video-signal sequences are coupled through a transmission channel 4 into a frequency filter 5. The frequency filter 5 modifies the spectral distribution of the video-signals present on the transmission channel 4 in accordance with its predetermined frequency response. The frequency response of the frequency filter 5 is chosen in accordance with the geometric dimensions of the interesting details on the radiograph 2, because by increasing the amplitudes of the high frequency components in the frequency spectrum, always smaller and smaller picture details will be emphasized or more sharply displayed. The increase of the lower frequency components and supression of the higher ones will result in the details having greater dimensions i.e. surfaces will be better outlined. The actual design of the frequency filter 5 will be described in a more detailed way in connection with FIGS. 3 and 4.

The video-signals of the so modified frequency spectrum are displayed on a monitor 6. As a result of the spectrum modification, this picture will have a different sharpness and structural richness than the original picture on the radiograph 2, but the brightness relations of the displayed picture will remain unchanged.

If besides or instead of the aforementioned picture detail sharpening method the brightness dynamic of the displayed picture is to be expanded, a dynamic corrector 7 is interposed between the monitor 6 and the video transmission channel 4.

The dynamic corrector 7 is shown by dotted lines in FIG. 1 showing that the use of the dynamic corrector is independent of the picture detail sharpening attained by the use of the frequency filter 5. The actual design of the dynamic corrector 7 will not be described because this circuit is known well in the art as a gamma corrector. For understanding the invention it is essential, however, to see the process clearly, by which to a given brightness range on the examined picture a wider intensity range on the monitor screen is assigned.

Figure 2:
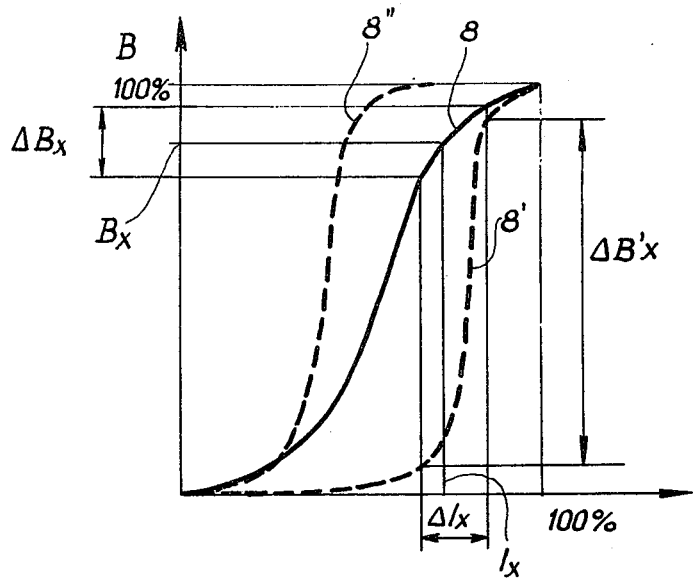
FIG. 2 is a diagrammatic representation of the relationship between a voltage proportional to the intensity of the examined picture and the light intensity of the displayed picture, demonstrating in this way the brightness dynamics expansion.

In FIG. 2 a curve 8 is plotted to illustrate this process. The curve 8 shows the functional relation between the video-detector output voltage and the light intensity or brightness B appearing on said monitor 6. Substantially the curve 8 is the exciting or driving characteristic of the monitor 6; on the horizontal voltage axis of the diagram each value corresponds to a given blackening or intensity I of the radiograph 2. The curve 8 can be therefore considered as a diagramatic representation of the function between the intensity I of the radiograph 2 and the brightness B of the picture on the monitor 6. It is supposed there is a detail on the radiograph 2 which is relevant from the evaluation and it has a total intensity range $\Delta I_x$ with a medium intensity $I_x$ also shown in the Figure.

The curve 8 shown with full line regards an application when the dynamic corrector 7 is not used.

To the intensity range $\Delta I_x$ corresponds on the vertical axis B a brightness range $\Delta B_x$ determined by the curve 8. Thus, the details relevant for the evaluation will take up only a relatively small part of the available full brightness range of the monitor. It is clear that if only the brightness or contrast of the monitor 6 is adjusted without any dynamic expansion, the relative width of the brightness range $\Delta B_x$ will not change, but only the intensity pertaining to the illumination of 100 percent (except the case of overdrive, which results in additional problems that are not particularized here). It can be seen therefore that the brightness or contrast adjustment used in the conventional systems is inadequate for the expansion of the intensity range $\Delta I_x$ which is important for the picture evaluation.

However, if the curve 8 is modified in accordance with a curve 8' represented by a dotted line on FIG. 2, e.g. by a suitable setting of the dynamic corrector 7, than an extended brightness range $\Delta B'_x$ will correspond to the original intensity range $\Delta I_x$ being relevant from medical aspects. Hereby the brightness dynamic of the original picture's relevant details is expanded on the displayed picture and the dynamic suppression of the irrelevant details renders possible a finer structural differentiation of the relevant details. For a man skilled in the art it is obvious that by changing the slope of the modified curve 8' the extent of dynamic expansion, while by shifting it parallel to the horizontal voltage axis, the medium brightness of the expanded range can be adjusted. In this way another curve 8'' also shown in FIG. 2 provides a similar dynamic expansion as the curve 8', but the medium brightness of the expanded range corresponds to a less lesser intensity on the radiograph 2 than in the first case e.g. to a more illuminated or brighter detail.

Thus, during the evaluation process the physician operating the system can display a picture with an extended brightness dynamic corrsponding to any optionally chosen intensity range on the examined radiograph 2 and this can be attained by a suitable adjustment of the slope and the horizontal position of the expansion curve 8' of the dymanic corrector 7.

Having now described the expansion method of the brightness dynamic, again reference is made to FIG. 1 and it is pointed out that the actual frequency response of the frequency filter 5 can be chosen from several known ones. The frequency dependent character of the frequency reponse is generatlly realized by using appropriately constructed four-terminal networks. However, the demand of the continous adjustment of the picture detail sharpening process makes it difficult to apply methods in which the frequency-dependent quadripole is connected in series with the transmission channel 4.

Figure 3:
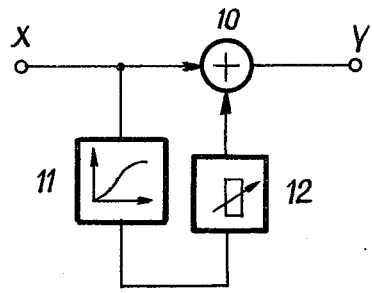
FIG. 3 is a schematic block diagram of a variant of a frequency filter in accordance with the invention.

In FIG. 3 a block diagram is shown, where points X and Y correspond to the input and output of the frequency filter 5, respectively. Thus to the video transmission channel 4 a first input of an adder 10 as well as an input of a frequency-dependent means 11 is coupled. The output of the adder 10 is coupled to point Y, which leads to the input of the monitor 6. Between a second input of the adder 10 and the free end of the frequency-dependent means 11 there is connected a frequency-independent level control circuit 12, e.g. an amplifier.

It is supposed that the frequency-dependent means 11 has a transfer function which is of sinusoidal distribution within the video range and that it has its maximum value at 5 Mc/s. There are two paths between point X and Y. In the first path a frequency-independent transmission is provided, while in the second path a frequency-dependent transmission occurs, e.g. a transmission having a sinusoidal distribution. By a continuous adjustment of the voltage level in the second path, with respect to that of the first one, the extent of the frequency-dependence can be controlled continuously without changing here the high frequency character of the resulting frequency response. The frequency-dependent means 11 can be realized by a low-pass filter, high-pass filter, band filter and comb filter, or by the combinationn of thereof. The actually used filter type must be chosen in accordance with the frequencies of the spectrum components to which the faint but relevant details of the examined picture are associated.

According to the most preferable solution the frequency response of the frequency-dependent means 11 can be continuously shifted along the frequency axis.

There is a condition of obtaining sharp pictures on the monitor, according to which the phase of the video-signal packet must be kept unchanged during the spectrum modification process, advisably it shall remain within limits of ±15°. As a frequency-dependent means therefore preferably means with compensated phase-shift must be selected.

Figure 4:
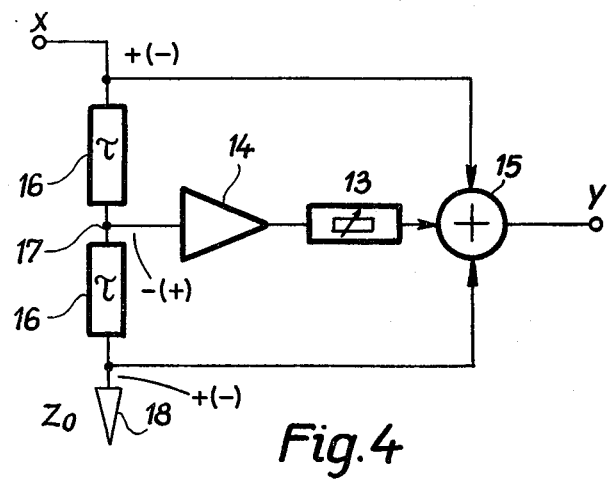
FIG. 4 is a schematic block diagram of another variant of the frequency filter.
Figure 2:
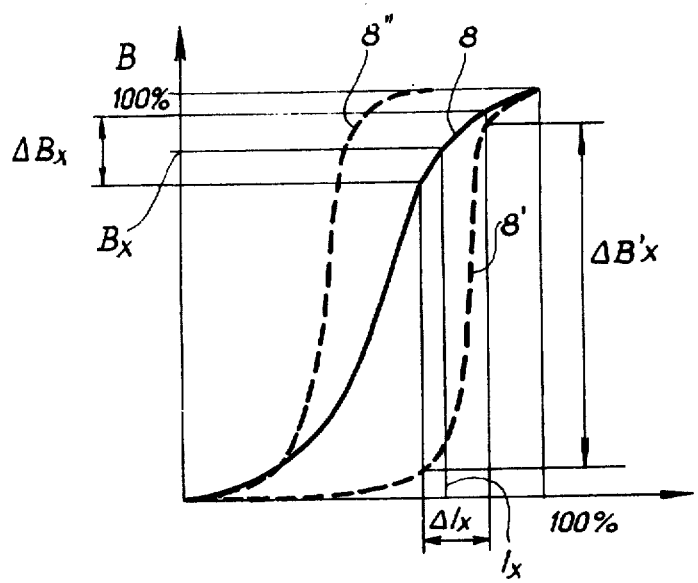
Figure 3:
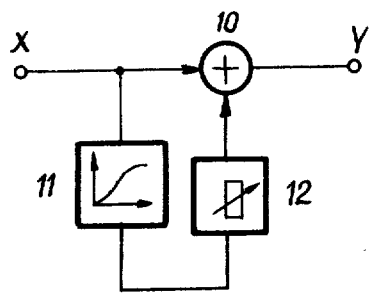
Figure 4:
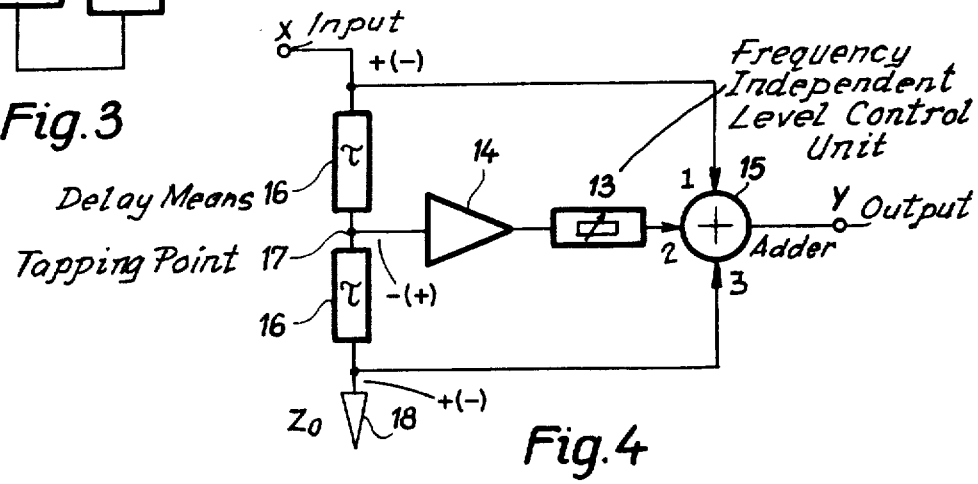

In connection with FIG. 4 a circuit arrangement is described, which satisfies the above condition and it is appropriate to emphasize any changes that take place in the video-signal sequence.

The contours of the faint or dim details on the examined picture always cause chanes in the sequence of the video-signals and the faint character can be considered as a consequence of the change.

The arrangement shown in FIG. 4 is similar to that shown in FIG. 3, but here a three-input adder 15 is used. Between the first and second inputs of the adder 15 a delay means 16 is connected. In the central zone, preferably in the centre of the delay means 16 there is a tap point 17. The tap point 17 is connected to the central or second input of the adder 15 through an inverter 14 and a frequency-independent level adjusting means 13. The inverter 14 and the linear level adjusting means 13 can also be built within a single stage. The delay means 16 is loaded at its terminal point by its characteristic impedance $Z_o$. The delay means 16 can of course be formed from two independent delay means, as well.

The operation of this arrangement is as follows:

Let us suppose that at point X a voltage signal appears. This voltage will reach the tap point 17 a time interval $\tau$ later, the third input of the adder after a time interval $2\tau$. The phase of the signals on the second input of the adder coming from the tap point 17 will be inverted, therefore in the adder this signal will be substracted from the sum of the signals present on the first and third inputs. Initially the examined signal at the output point Y increases, but due to the activization of the second input, a time interval $\tau$ later this increase will lessen, stop or decrease in time, this effect of the signal on the second input depends on the attenuation or gain of the frequency-independent level adjusting means 13. After a time interval $2\tau$ the increasing signal reaches the third input and it increases again the output voltage. Depending on the chosen time interval $\tau$ and on the gain or attenuation inserted into the path leading to the second input, the original change in the video-signal will be emphasised at point Y as to become a characteristic and easily noticable voltage change, having at least one steep section. This steep voltage change provides, on the screen of the monitor 6, visual information which is easily evaluated by the viewer. By a continuous adjustment of the delay time $\tau$ of the delay means 16 it is possible to change the width of the emphasized slope and as a consequence thereof the size of the emphasised picture detail can also be adjusted.

If the invention is used for an X-ray examination, it decreases the required amount of radiation dosage decreasing thereby also the radiation load both on the examined patient and on the personnel carrying out this examination. The amount of the required dosage will be considerably decreased with respect to that applied by the conventional systems using picture amplifiers, though these conventional systems required already a less dosage than the X-ray systems using fluorographic display. Depending on the character of the examination good results have been experienced with the system according to the invention using X-ray dosages ranging between 20–70% of the dosages used by the systems with picture amplifier. The medical and health consequences of the dosage decrease lead to invaluable advantages.

Besides the above described embodiments of the invention given as examples only, people skilled in the art will be able to use the invention in several other forms, so it should not be limited to the described embodiments. The invention shall be limited only by the scope of the claims.

What we claim is:

1. In a circuit arrangement for the transmission of picture details through a video chain for the emphasis of blurred contours, the arrangement being connected in series with a section serving for the transmission of video signals separated from synchronous signals of the video chain; the improvement in which the circuit contains delay means having a tapping point, an adder, a frequency-independent level control unit by which the input of the delay means is connected to a first input of the adder, the frequency-independent level control unit being connected between the tapping point and a second input of the adder, the output of the delay means being connected to a third input of the adder, the first and third inputs of the adder belonging to an operation having a common sign, opposite to that of the second input, the circuit input being formed by an input of the delay means, the circuit output being formed by the output of the adder.

2. A circuit arrangement according to claim 1, in which the delay time of the delay means may be varied.

3. Circuit arrangement according to claim 1, in which in order to keep the phase-displacement within ± 15°, the delay means are formed by two delay lines, connected in series and having identical delay times, the output being connected to the adder.

4. A circuit arrangement according to claim 3, in which between the tapping point and the second input of the adder an inverter stage is connected.

* * * * *

UNITED STATES PATENT AND TRADEMARK OFFICE
CERTIFICATE OF CORRECTION

PATENT NO. : 3,969,571
DATED : July 13, 1976
INVENTOR(S) : Martha FENYO

It is certified that error appears in the above-identified patent and that said Letters Patent are hereby corrected as shown below:

In the Abstract, line 8, change "that connects the" to --. The--;

line 9, after "means" insert --is connected--.

Claim 1, line 8, change "by which" to a comma (,);

line 9, change "is" to --being--.

Sheet 2 of the drawings should appear as per attachment.

Signed and Sealed this

Twenty-eighth Day of February 1978

[SEAL]

Attest:

RUTH C. MASON
Attesting Officer

LUTRELLE F. PARKER
Acting Commissioner of Patents and Trademark